(12) United States Patent
Neergaard et al.

(10) Patent No.: US 10,945,949 B2
(45) Date of Patent: Mar. 16, 2021

(54) MEDICAL CHEWING GUM COMPRISING CANNABINOID

(71) Applicant: NordicCan A/S, Vejle (DK)

(72) Inventors: Jesper Neergaard, Aabenraa (DK); Anayo Ogbonna, Brønshøj (DK)

(73) Assignee: NordicCan A/S

( * ) Notice: Subject to any disclaimer, the term of this patent is extended or adjusted under 35 U.S.C. 154(b) by 14 days.

(21) Appl. No.: 15/766,712

(22) PCT Filed: Oct. 7, 2015

(86) PCT No.: PCT/DK2015/050300
§ 371 (c)(1),
(2) Date: Jul. 31, 2018

(87) PCT Pub. No.: WO2017/059859
PCT Pub. Date: Apr. 13, 2017

(65) Prior Publication Data
US 2019/0060229 A1 Feb. 28, 2019

(51) Int. Cl.
| | | |
|---|---|---|
| *A61K 9/68* | (2006.01) | |
| *A61K 9/16* | (2006.01) | |
| *A61K 9/20* | (2006.01) | |
| *A61K 31/352* | (2006.01) | |
| *A61K 31/05* | (2006.01) | |
| *A61K 47/32* | (2006.01) | |
| *A61K 47/38* | (2006.01) | |

(52) U.S. Cl.
CPC .......... *A61K 9/0058* (2013.01); *A61K 9/1635* (2013.01); *A61K 9/2027* (2013.01); *A61K 9/2077* (2013.01); *A61K 31/05* (2013.01); *A61K 31/352* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 2011/0097283 A1* | 4/2011 | Van Damme | ........ A61K 9/0058 424/48 |
| 2013/0309352 A1* | 11/2013 | Wimmer | ................ C08L 31/04 426/4 |

FOREIGN PATENT DOCUMENTS

| | | | |
|---|---|---|---|
| WO | 2004004479 A1 | 1/2004 | |
| WO | 2009120080 A1 | 10/2009 | |
| WO | WO-2009120080 A1 * | 10/2009 | ........... A61K 9/0058 |

OTHER PUBLICATIONS

Avicel PH 102 prodcut information sheet, 2005, pp. 1-2. (Year: 2005).*

* cited by examiner

*Primary Examiner* — Brian Gulledge
(74) *Attorney, Agent, or Firm* — St. Onge Steward Johnston & Reens LLC

(57) ABSTRACT

A medical chewing gum including gum base polymers and one or more cannabinoids as an active pharmaceutical ingredient, the gum base polymers including polyvinyl acetate and vinyl laurate-vinyl acetate copolymer in an amount of more than 90% by weight of the gum base polymers, wherein the gum base polymers include 20-95% by weight of polyvinyl acetate and 5-80% by weight of vinyl laurate-vinyl acetate copolymer.

27 Claims, 1 Drawing Sheet

MEDICAL CHEWING GUM COMPRISING CANNABINOID

FIELD OF THE INVENTION

Figure 1:
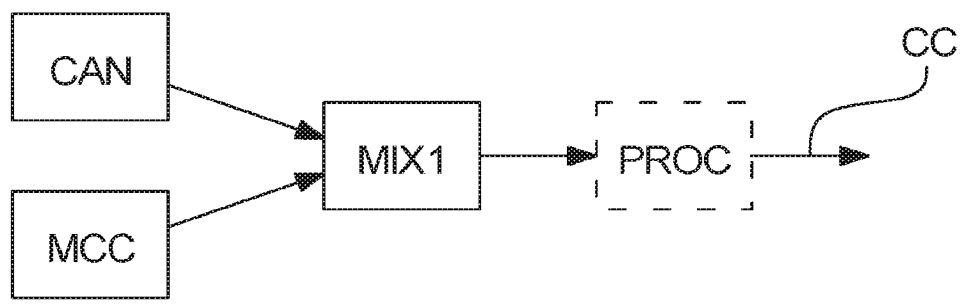

The invention relates a medical chewing gum, a medical chewing gum for use in pain alleviation and methods of dosing cannabinoid to a chewing gum.

BACKGROUND OF THE INVENTION

Cannabinoids or derivatives thereof have been used for medical purposes. The medical purposes include different types of pain relief, for counteracting side effects in relation cancer treatment such as nausea and vomiting, treatment or counteracting side effects of different types of illnesses. Such treatment is very often limited to relatively critical diseases due to the fact than most countries regard recreational use to be illegal.

The administration may therefore be evaluated differently than just ensuring that the active constituents are somehow induced into the blood. Further considerations may be applicable.

One way of administering the active constituents is by inhalation or smoking. A problem related to such administration is that the rapid absorption into the blood via the lung may be undesirable. Not only may the smoking as such have side effects, but the administration may be difficult to manage.

Another administration method may include the use of medical tablets which are intended to be swallowed by the patient and where the active constituent is released in the stomach of the patient. A challenge in relation to such use is that the tablets has a very low bio-availability and also that patients receiving complex tablet treatment including several different types of tablets simply have difficulties in swallowing the tablets.

WO 2009/120080 discloses the use of chewing gum as a medical carrier and release vessel of cannabinoids. The chewing gum may facilitate a prolonged release of cannabinoids compared to other types administering methods. A problem related to the indicated administration method is that indicated solution is relatively costly. Another problem is that this type of administration is somewhat problematic with respect to taste masking.

One challenge of medical chewing gum in general is that the chewing gum is a complex delivery vehicle. Chewing gum or gum base ingredients may affect multiple properties of the chewing gum. One such example may be that the application of a particular gum base or chewing gum ingredient softens the chewing gum, thereby leading to an increased release due to the eased chewing of the chewing gum. This may be attractive or non-attractive, but a challenge is that the release may be different from the release induced by another ingredient and most of all, the chewing gum texture may simultaneously be affected to a degree that the chewing gum does not have the desired typical textural chewing gum properties. This may e.g. be counteracted by the incorporation of another chewing gum ingredient making the chewing gum harder and/or increasing the elasticity, but this may then affect the desired release and so forth. When referring to typical textural chewing gum properties, it is here noted that the desired rheology of chewing gum is very different from the rheology of typical chewy confectionery such as toffee, chocolate, wine gum, etc. This is in particular the case in relation to the elastomeric properties required to obtain a confectionery product satisfying the consumer's expectations in relation to a chewing gum.

A further challenge in relation to cannabinoid chewing gum is that the cannabinoid released may cause an unpleasant sensory sensation for the user of the chewing gum. On the other hand there is a desire to maximize the cannabinoid release from the chewing gum, as it is this cannabinoid which provides the user of the chewing gum the desired medical effect.

In other words, the cannabinoid should be released, but at the same time the cannabinoid released causes a high perception of bitterness.

SUMMARY OF THE INVENTION

The invention relates to a medical chewing gum comprising gum base polymers and one or more cannabinoids as an active pharmaceutical ingredient, the gum base polymers comprising polyvinyl acetate and vinyl laurate-vinyl acetate copolymer in an amount of more than 90% by weight of the gum base polymers, wherein the gum base polymers include 20-95% by weight of polyvinyl acetate and 5-80% by weight of vinyl laurate-vinyl acetate copolymer.

A significant advantage of the present invention is that the cannabinoid(s) may have a significantly better release profile than with existing conventional gum base. A significantly better release in this context refers to the absolute amount of cannabinoid(s) released from the chewing gum over a realistic chewing period.

Then present gum base may also offer a possibility of an improved taste masking in the sense that the gap between release of the cannabinoid(s) and the taste masking ingredients may be overall reduced.

Another important result of the specific combination of cannabinoid(s) and gum base polymers is that a reduced amount of cannabinoid(s) will reduce the requirements for taste masking, or alternatively make the taste masking more efficient. This is extremely important given the fact that many seriously ill patients may have difficulties in coping with the taste of cannabinoid.

One advantage of the invention may be that cannabinoid may be delivered to the oral cavity by means of the claimed very attractive chewing gum platform with a reduced unpleasant taste perceived in the oral cavity of the user when compared to the unpleasant taste perceived by means of comparable cannabinoid release of a conventional chewing gum formulation. This is contrary to the expectations that an increased release would lead to an increased unpleasant taste or that a comparable release would lead to a comparable discomfort in relation to taste. It should be noted that bitterness induced by cannabinoid represents an unpleasant taste.

It should also be noted that this unexpected effect is very attractive in relation to medicated chewing gum in the present context as a large group of the patients who may benefit from the inventive chewing gum will be very vulnerable to bad taste such as bitterness due to the fact that some of these patient also may suffer from reduced appetite.

In an embodiment of the invention the total content of gum base ingredients selected from the list consisting of polyterpene resins, resins based on gum rosin, wood rosin and tall oil resin is less than 5 percent by weight of the chewing gum such as less than 3 percent by weight of the chewing gum, such as less than 2 percent by weight of the chewing gum, such as less than 1 percent by weight of the chewing gum, such as less than 0.5 percent by weight of the chewing gum, such as less than 0.2 percent by weight of the chewing gum.

For example the total content of polyterpene resins, resins based on gum rosin, wood rosin and tall oil resin is 0 percent by weight of the chewing gum, i.e. the chewing gum contains no polyterpene resins and no resins based on gum rosin, wood rosin or tall oil resin.

In an embodiment of the invention the chewing gum contains no polyterpene resins and no resins based on gum rosin, wood rosin or tall oil resin.

In an embodiment of the invention the chewing gum is compressed chewing gum.

A compressed chewing gum is typically formed by compression of granules containing gum base. These gum base granules may comprise gum base only or e.g. comprise further chewing gum ingredients than the gum base, such as flavor(s), sweeteners, etc. The gum base granules, with or without further chewing gum ingredients mixed into the gum base of the granules may be compressed directly into a compressed chewing gum. As an alternative, the finished gum base granules may also be physically mixed with chewing gum ingredients into a mixture of discrete gum base granules and particles of chewing gum ingredients and then be compressed into a final compressed chewing gum.

When applying a compressed chewing gum as a vehicle the total release will typically be faster and better and there will be more options of providing an appropriate taste masking.

This is in particular relevant in relation to the cannabinoids and the initial "crumbling" of chewing gum facilitates an increased total release when compared to conventional extruded chewing gum. This is the case regardless of whether the cannabinoid is included in gum base granules or whether it is added to the chewing gum composition as particles which may be compressed together with gum base granules.

In an embodiment of the invention the compressed chewing gum comprises a chewing gum composition, wherein the chewing gum composition comprises gum base granules and wherein the one or more cannabinoids is a least partly comprised in said gum base granules.

An advantageous release of the cannabinoid may be obtained if including the cannabinoid in small particles even if cannabinoid is mixed with gum base in these particles. The release is of course prolonged compared to release from a chewable tablet without gum base, but the particular containing of cannabinoids will provide a faster release over conventional extruded chewing gum.

In an embodiment of the invention the compressed chewing gum comprises a chewing gum composition, wherein the chewing gum composition comprises gum base granules and wherein the one or more cannabinoids is contained in said gum base granules.

Keeping the at least one cannabinoid in the gum base may decrease the risk of segregation during an alternative compression process.

In an embodiment of the invention the compressed chewing gum comprises a chewing gum composition, wherein the chewing gum composition comprises gum base granules and wherein the one or more cannabinoids is a least partly comprised in the chewing gum composition outside the gum base granules.

An improved traceability may be obtained when keeping the cannabinoid in the particles without chewing gum base. A further advantage is that the cannabinoids are released relatively fast when compared to cannabinoid contained in gum base granules of a compressed chewing gum or cannabinoid mixed into a conventionally mixed chewing gum.

A further advantage is that the cannabinoid reacts less with the gum base of the chewing gum when compared to a conventionally mixed chewing gum. This may both have an impact on the visual appearance of the product and it may also have an impact on the intended effect of the medicated chewing gum or the stability of cannabinoid when it is mixed into the gum base.

In an embodiment of the invention the chewing gum comprises a chewing gum composition, wherein the chewing gum composition comprises gum base granules and wherein the one or more cannabinoids is a least partly comprised in the chewing gum composition outside the gum base granules and wherein the one or more cannabinoids is adsorbed to or coated onto the gum base granules prior to compression.

In an embodiment of the invention, the compressed chewing gum comprises a chewing gum composition, wherein the chewing gum composition comprises gum base granules and wherein the one or more cannabinoids is comprised in the chewing gum composition outside the gum base granules.

In an embodiment of the invention, the compressed chewing gum comprises a chewing gum composition, wherein the chewing gum composition comprises gum base granules and wherein the one or more cannabinoids is a least partly comprised in said gum base granules and at least partly comprised in the chewing gum composition outside the gum base granules.

When adding cannabinoids to the particles containing chewing gum and also adding it in particles free of gum base, it may be possible to adapt the desired release without releasing too much in the beginning of the chewing process or keeping too much cannabinoid in the chewing gum subsequent to chewing. In other words, it may be possible to prolong the release to obtain in improved bio-availability and at the same time minimize the amount of cannabinoid wasted due to the fact that the chewing gum is disposed by the user before the chewing has released the content of cannabinoids.

In an embodiment of the invention the medical chewing gum comprises two or more modules.

In an embodiment of the invention, the one or more cannabinoids is contained in one of the modules.

The administration and manufacturing of the chewing gum may be eased and optimized for the addition of cannabinoid due to the fact that a part of the chewing gum, e.g. one module of a two-module chewing gum may be produced conventionally with sweeteners, flavors, texture forming components, etc. under "normal" procedural control.

In an embodiment of the invention the medical chewing gum comprises gum base granules, said gum base granules comprising gum base polymers.

In an embodiment of the invention the gum base granules comprises further ingredients other than gum base polymers.

In an embodiment of the invention the gum base granules have an average diameter below 2 millimeters, such as between 0.01 and 2 millimeters, such as between 0.1 and 2 millimeters.

In an embodiment of the invention the gum base granules comprises gum base polymers in an amount of 0.1 to 99% by weight of the gum base granules.

In an embodiment of the invention the one or more cannabinoids comprises THC, CBD, salts and derivatives thereof, including analogues and homologues.

In an embodiment of the invention said chewing gum comprises said cannabinoids in an amount of 0.1-30 mg, such as 1-20 mg, such as 5-15 mg.

In an embodiment of the invention said one or more cannabinoids comprises tetrahydrocannabinol (THC).

Preferably THC is intended to mean (−)-trans-$\Delta^9$-tetrahydrocannabinol, i.e. (6aR,10aR)-delta-9-tetrahydrocannabinol).

In an embodiment of the invention said one or more cannabinoids comprises cannabidiol (CBD).

In an embodiment of the invention said one or more cannabinoids comprises a combination of several cannabinoids, such as THC and CBD.

In an embodiment of the invention said one or more cannabinoids is THC.

In an embodiment of the invention said one or more cannabinoids is CBD. In an embodiment of the invention said one or more cannabinoids is a combination of THC and CDB.

In an embodiment of the invention said one or more cannabinoids is for use in pain alleviation.

In an embodiment of the invention the one or more cannabinoids is at least partly contained in a carrier.

In an embodiment of the invention the chewing gum comprises cellulose as a carrier for said one or more cannabinoids.

Thus, according to the above embodiment the chewing gum comprises cellulose as a carrier for the cannabinoids; the cellulose as carrier will also be referred to as carrier cellulose.

Carrier cellulose as particles are well suited for mixing into conventionally mixed, batch or extruded chewing gum, but the articles are in particular well suited for compression due to the fact that the particles may be functionally included in the chewing gum by a simple compression at low temperatures and also due to the fact that paste or more liquid substances is extremely difficult to handle in relation to compressed chewing gum.

Other suitable carriers which may be employed in combination with or as an alternative to cellulose includes, but not limited to polysaccharides, oligosaccharides, polyols, polyamino acid, surfactants, fatty acids and salts and their derivatives including short and medium chain triglycerides, vegetable oils, triacetin, cyclodextrins, and oil flavors. Oil flavor may e.g. include mint oil In an embodiment of the invention the carrier cellulose is or comprises microcrystalline cellulose.

It should be understood in connection with the above embodiment that the medical chewing gum may in some embodiments comprise further cellulose, which is not microcrystalline cellulose; this may e.g. be cellulose as filler. However, in other embodiments, all the cellulose of the medical chewing gum is microcrystalline cellulose.

One advantage of the above embodiment may be that microcrystalline cellulose may absorb a relatively high amount of cannabinoid, while also allowing for the one or more cannabinoids to be effectively released from the medical chewing gum when chewed.

In an embodiment of the invention said carrier cellulose is provided in the form of particles having an average particle size between 10 and 250 micrometers, such as between 15 and 200 micrometers, such as between 20 and 150 micrometers, such as between 50 and 100 micrometers, such as about 75 micrometers.

In an embodiment of the invention said carrier cellulose has a specific surface area of between 0.65 and 1.5 $m^2/g$, such as between 0.75 and 1.25 $m^2/g$, such as between 0.85 and 1.15 $m^2/g$, such as between 0.9 and 1.1 $m^2/g$, such as about 0.95 $m^2/g$, about 1.00 $m^2/g$, or such as about 1.05 $m^2/g$.

In an embodiment of the invention said carrier cellulose has a bulk density between 0.1 and 1.0 grams per cubic centimeter ($g/cm^3$), such as between 0.25 and 0.5 grams per cubic centimeter, such as between 0.26 and 0.31 grams per cubic centimeter, or such as between 0.28 and 0.33 grams per cubic centimeter.

In the context of the above embodiment it should preferably be understood that the bulk density of the carrier cellulose is understood as the bulk density at about 25 degrees Celsius.

In an embodiment of the invention said carrier cellulose has a porosity characterized by an average specific pore volume between 0.003 $cm^3/g$ and 0.60 $cm^3/g$, such as between 0.01 and 0.3 $cm^3/g$.

In an embodiment of the invention said carrier cellulose has a moisture content of less than about 5% by weight, such as between 2 and 5% by weight, such as between 3 and 5% by weight, such as about 4% by weight.

In an embodiment of the invention a weight-ratio between the one or more cannabinoids and the carrier cellulose is between 1:1000 and 1:1, such as between 1:500 and 1:50.

In an embodiment of the invention said carrier cellulose is selected from the list consisting of microcrystalline cellulose (MCC); carboxymethylcellulose (CMC), such as sodium carboxymethylcellulose; hydroxypropyl methylcellulose (HPMC); methylcellulose; ethylcellulose (EC); methylethylcellulose (MEC); hydroxyethyl cellulose (HEC); hydroxyethyl methylcellulose (HEMC); and any combination thereof.

In an embodiment of the invention said medical chewing gum comprises carrier cellulose in an amount of 0.1 mg to 8 mg.

In an embodiment of the invention said carrier cellulose has an average fiber size of less than 200 micrometers, such as between 75 and 125 micrometers, or such as below 75 micrometers.

In an embodiment of the invention the carrier cellulose comprises pores, the pores having an average pore size of between about 3 nanometers and about 300 nanometers, such as between 10 nanometers and 200 nanometers, such as between 20 nanometers and 100 nanometers.

In an embodiment of the invention said carrier cellulose is derived from natural sources, such as wood pulp.

Other examples of natural sources of cellulose include sugar beet fiber, cotton fiber, bran fiber, citrus pulp fiber, grass fiber, willow fiber, poplar fiber, bamboo fiber, and combinations thereof, or combinations thereof with wood pulp.

In some embodiments the carrier cellulose y be chemically treated, e.g. by means of CMC, MPMC, HPC, MCC, and/or other methods.

Alternatively, the cellulose may be semi-synthetic or synthetic cellulose.

In an embodiment of the invention said carrier cellulose is added to the one or more cannabinoids before it is added to the chewing gum.

In an embodiment of the invention said medical chewing gum comprises one or more fillers.

In an embodiment of the invention said one or more fillers comprise filler cellulose.

In accordance with the above embodiment, it should be understood that typical cellulose types may be used as filler cellulose. In some embodiments some or all of the filler cellulose is of the same type as some or all of the carrier cellulose.

In an embodiment of the invention the chewing gum comprises one or more fillers including magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, starch polymers, fibers and combinations thereof.

In an embodiment of the invention the filler is calcium carbonate, talc, cellulose polymers or combinations thereof.

In an embodiment of the invention the filler is present in an amount of 5-45% by weight of the chewing gum, such as in an amount of 10-40% by weight of the chewing gum.

In an embodiment of the invention the medical chewing gum is substantially free of natural resins.

In an embodiment of the invention the chewing gum comprises gum base polymers in an amount of between 15 and 80 percent by weight of the chewing gum, such as between 20 and 60 percent by weight of the chewing gum, such as between 30 and 50 percent by weight of the chewing gum, such about 35, about 40, or about 45 percent by weight of the chewing gum.

In an embodiment of the invention the gum base polymers consists of synthetic gum base polymers.

In an embodiment of the invention the weight ratio between polyvinyl acetate and vinyl laurate-vinyl acetate copolymer is from 8:1 to 2:3.

In an embodiment of the invention the weight ratio between polyvinyl acetate and vinyl laurate-vinyl acetate copolymer is from 5:1 to 2:3.

In an embodiment of the invention the weight ratio between polyvinyl acetate and vinyl laurate-vinyl acetate copolymer is from 3:2 to 2:3.

In an embodiment of the invention the weight ratio between vinyl acetate monomers of vinyl laurate-vinyl acetate copolymer and vinyl laurate monomers of vinyl laurate-vinyl acetate copolymer is less than 90:10, such as 80:20, such as 60:40.

In an embodiment of the invention the weight-average molecular weight Mw of polyvinyl acetate is from 5,000 to 120,000, such as 5,000 to 70,000, such as 7,000 to 25,000, and the weight-average molecular weight Mw of vinyl acetate-vinyl laurate copolymer is from 80,000 to 700,000, such as 100,000 to 600,000, such as 120,000 to 250,000.

In an embodiment of the invention the weight-average molecular weight Mw of polyvinyl acetate is from 5,000 to 120,000, such as 5,000 to 70,000, such as 7,000 to 25,000.

In an embodiment of the invention the weight-average molecular weight Mw of vinyl acetate-vinyl laurate copolymer is from 80,000 to 700,000, such as 100,000 to 600,000, such as 120,000 to 250,000.

In an embodiment of the invention the chewing gum comprises a plasticizer.

In an embodiment of the invention the chewing gum comprises wax.

In an embodiment of the invention the chewing gum comprises fat.

In an embodiment of the invention the chewing gum comprises an emulsifier.

In an embodiment of the invention the synthetic gum base polymers are forming part of a gum base.

In an embodiment of the invention the gum base comprises 15-45% by weight of polyvinyl acetate, 10-30% by weight of vinyl laurate-vinyl acetate copolymers, 15-45% by weight of fillers, 5-30% by weight of waxes or fats, 1-10% by weight of plasticizers and 1-10% by weight of emulsifiers.

In an embodiment of the invention the gum base comprises 20-35% by weight of polyvinyl acetate, 12-25% by weight of vinyl laurate-vinyl acetate copolymer, 20-30% by weight of fillers, 10-20% by weight of waxes or fats, 2-8% by weight of plasticizers and 2-8% by weight of emulsifiers.

In an embodiment of the invention the gum base polymers further comprises one or more elastomers selected from the group consisting of styrene-butadiene copolymers (SBR), polyisobutylene, isobutylene-isoprene copolymers, polyethylene, polyurethane or any combination thereof.

In an embodiment of the invention the gum base polymers further comprises one or more elastomers in an amount of 0.1-10% by weight, such as in an amount of 1-8% by weight, such as in an amount of 1.5-6% by weight.

In an embodiment of the invention the chewing gum comprises emulsifiers in an amount of 0.1% to 25% by weight of said chewing gum, such as 1-10% by weight of said chewing gum, such as 2-8% by weight of said chewing gum.

In an embodiment of the invention the emulsifiers are selected from the group of acetylated monoglycerides, mono- and/or di-glycerides of fatty acids such as glycerol monostearate, acetem, lecithines and any combination thereof.

In an embodiment of the invention the plasticizer comprises diacetin and/or triacetin.

In an embodiment of the invention the plasticizer comprises glycerol and/or medium chain triglycerides.

In an embodiment of the invention the waxes are selected from the group consisting of paraffin waxes, microcrystalline waxes, polyethylene waxes and natural waxes.

In an embodiment of the invention the fats are selected from the group consisting of animal fats and vegetable fats.

In an embodiment of the invention the chewing gum comprises flavor in an amount between 0.01 and 10% by weight of the chewing gum such as in an amount between 0.01 and 5% by weight of the chewing gum.

According to an advantageous embodiment of the invention, the chewing gum may be formulated with flavors, e.g. flavors including acids, which may be more acceptable for seriously ill patients, such as patients receiving chemotherapy.

In an embodiment of the invention the chewing gum comprises high intensity sweetener.

In an embodiment of the invention the chewing gum comprises bulk sweeteners including sugar and/or sugarless components.

In an embodiment of the invention the chewing gum comprises bulk sweetener in an amount of 5 to about 95% by weight of the chewing gum, more typically 20 to about 80% by weight, and more commonly, 30 to 60% by weight of the chewing gum.

In an embodiment of the invention the synthetic gum base polymers are resins and elastomers.

In an embodiment of the invention the chewing gum is free of antioxidants.

In an embodiment of the invention the chewing gum comprises gum base in an amount of 30-75% by weight of the chewing gum before any optionally applied coating, such as 35-70% by weight of the chewing gum or 40-65% by weight of the chewing gum or 45-60% by weight of the chewing gum.

In an embodiment of the invention the chewing gum is manufactured in a two-step process, the first step including the process of providing gum base in a first mixing process and a further step including the process of mixing gum base with further chewing gum components in a further mixing process.

In an embodiment of the invention the chewing gum is manufactured in a one step process by means of an extruder.

In an embodiment of the invention the medical chewing gum has a tan (delta) of at less than 1.2, such as less than 1.1, such as less than 1.0.

In an embodiment of the invention the medical chewing gum has a tan delta of at less than 1.2, such as less than 1.1, such as less than 1.0 wherein said tan (delta) is measured at an oscillation frequency of frequency of approximately 1 Hz.

In an embodiment of the invention the medical chewing gum has a tan delta of at less than 1.2, such as less than 1.1, such as less than 1.0 wherein said tan (delta) is measured at an oscillation frequency of frequency of approximately 1 Hz and wherein said tan delta is measured at an oscillation torque of about 8 to 12 μN·m.

In an embodiment of the invention the medical chewing gum has a tan delta of at less than 1.2, such as less than 1.1, such as less than 1.0 wherein said tan (delta) is measured at an oscillation frequency of frequency of approximately 1 Hz and wherein said tan delta is measured at an oscillation torque of about 8 to 12 μN·m and wherein said tan delta is measured by AR 1000 rheometer from TA Instruments and at a temperature of 37° C.

In an embodiment of the invention the medical chewing gum has a tan delta of less than 1.2, such as less than 1.1, such as less than 1.0 wherein said tan (delta) is measured at an oscillation frequency of frequency of approximately 1 Hz and wherein said tan delta is measured at an oscillation torque which provides a linear viscoelastic response (LVR).

In an embodiment of the invention the medical chewing gum has a tan delta of at less than 1.2, such as less than 1.1, such as less than 1.0 wherein said tan (delta) is measured at an oscillation frequency of frequency of approximately 1 Hz and wherein said tan delta is measured at an oscillation torque which provides a linear viscoelastic response (LVR) and wherein said tan delta is measured by AR 1000 rheometer from TA Instruments and at a temperature of 37° C.

In an embodiment of the invention the tan (delta) is defined as (loss modulus G"/storage modulus G').

In an embodiment of the invention the gum base polymers comprise natural gum base polymers in an amount less than 1% by weight, preferably less than 0.5% by weight, more preferably less than 0.2% by weight, most preferably less than 0.1% by weight.

Moreover, the invention relates to a medical chewing gum for use in pain alleviation treatment, the medical chewing gum comprising gum base polymers and one or more cannabinoids as an active pharmaceutical ingredient, the gum base polymers comprising polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer.

In an embodiment of the invention the chewing gum use in pain alleviation treatment contains no polyterpene resins and no resins based on gum rosin, wood rosin or tall oil resin.

Embodiments of the invention includes chewing gum according to any of the claims 1-88 for use in pain alleviation treatment according to claim 89 or 90.

Moreover, the invention relates to a method of dosing one or more cannabinoids to a chewing gum, wherein the chewing gum comprises a chewing gum composition, wherein the chewing gum composition comprises gum base granules and particles free of gum base, and wherein the one or more cannabinoids is contained in the particles free of gum base and wherein the particles free of gum base are mixed with gum base granules and compressed to form a chewing gum tablet.

In an embodiment of the invention wherein the chewing gum comprises gum base polymers, wherein the gum base polymers comprises polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer.

In an embodiment of the invention the gum base polymers comprises polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer, and wherein the chewing gum contains no polyterpene resins and no resins based on gum rosin, wood rosin or tall oil resin Embodiments include dosing one or more cannabinoids to a chewing gum according to any of the claims 92-94 and wherein the chewing gum is formulated according to any of claims 1-88.

Moreover, the invention relates to a method of dosing one or more cannabinoids to a chewing gum, wherein the chewing gum comprises a chewing gum composition, wherein the chewing gum composition comprises gum base granules, and wherein the one or more cannabinoids is mixed into the gum base granules and compressed to form a chewing gum tablet.

In an embodiment of the invention the chewing gum comprises gum base polymers, wherein the gum base polymers comprises polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer.

In an embodiment of the invention the gum base polymers comprises polyvinyl acetate and vinyl laurate-vinyl acetate copolymer in an amount of more than 90% by weight, wherein the gum base polymers include 20-95% by weight of polyvinyl acetate and 5-80% by weight of vinyl laurate-vinyl acetate copolymer, and wherein the chewing gum contains no polyterpene resins and no resins based on gum rosin, wood rosin or tall oil resin Embodiments include methods of dosing one or more cannabinoids to a chewing gum according to any of the claims 96-98 and wherein the chewing gum is formulated according to any of claims 1-88.

THE FIGURES

The invention will now be described with reference to drawings, where

Figure 2:
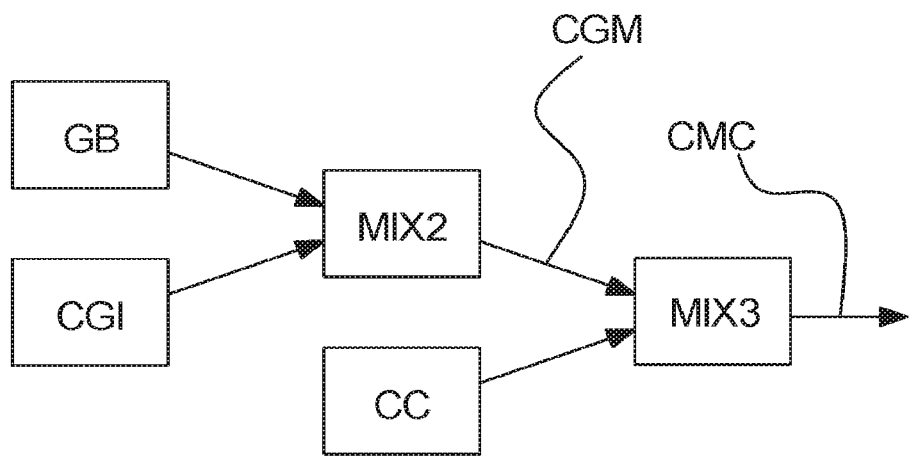

FIG. 1 illustrates a method of preparing a cannabinoid-microcrystalline cellulose mixture according to an embodiment of the invention and where FIG. 2 illustrates a process for preparing chewing gum mass with cannabinoid-microcrystalline cellulose CMC according to an embodiment of the invention

DEFINITIONS

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one". Additionally, the words "a" and "an" when used in the present document in concert with the word comprising or containing denote "one or more."

As used herein, by the phrase "chewing gum" is meant any chewing gum such as extruded chewing gum, center-filled chewing gum, toffee-imitating chewing gum, or compressed chewing gum, slabs or sticks.

By the terms "gum base" and "gum base matrix" is meant the mainly water-insoluble and hydrophobic gum base ingredients that are mixed together, typically before the bulk portion of the chewing gum is added. The "gum base" may contain gum base polymers and plasticizers, waxes, emulsifiers, fats and/or fillers. The gum base may thus designate the typical water-insoluble chewing gum components, which may be manufactured in a first step and subsequently mixed with the mainly water soluble portion in a second step. The term gum base may, evidently, also refer to the relevant gum base components fed into an extruder and forming part of the final chewing gum when mixed with the chewing gum components in the extruder.

The term "bulk portion" intends to mean the mainly water-soluble and hydrophilic chewing gum ingredients that may be mixed into the gum base matrix, either in a separate process or in a one-step process by means of an extruder.

The term "gum base polymer" intends to mean resins and elastomers of polymeric origin and does not include, for example, plasticizers, waxes, emulsifiers, fats or fillers although these may also be present in a gum base.

The term "weight of the chewing gum" or similar wording meaning the same is defined in the present context as weight of the chewing gum, not including the weight of an outer coating, such as a hard coating, soft coating, and the like.

By the phrase "texture" is meant a qualitative measure of the visco-elastic properties of the chewing gum and of the overall mouth-feel experienced by the user during the chewing process. Thus the term "texture" encompasses measurable quantities such as hardness and elasticity as well as more subjective parameters related to the chew-feel experienced by a user.

The term "natural resin", as used herein, means resinous compounds being either polyterpenes derived from terpenes of natural origin or resinous compounds derived from gum rosin, wood rosin or tall-oil rosin.

The term "synthetic polymer", as used herein, means polymers industrially synthesized by appropriate polymerization techniques.

The term "buffer", as used herein, refers to pH-control agents.

The average particle size is understood to mean the D50 value as measured by laser diffraction analysis The term "bitterness" should be understood as the taste of bitterness, and as being evaluated by a taste panel of 4 persons trained for sensory evaluation. The trained persons chewed the samples at a rate of 60 chews per minute and for each sample evaluated bitterness.

DESCRIPTION

According to embodiments of the invention a preferred amount of gum base matrix in the final chewing gum is 30-75% by weight of the chewing gum before any optionally applied coating, such as 35-70% by weight of the chewing gum or 40-65% by weight of the chewing gum or 45-60% by weight of the chewing gum.

The formulation of gum bases can vary depending on the particular product to be prepared and on the desired masticatory and other sensory characteristics of the final product.

Besides the polyvinyl acetate and the vinyl laurate-vinyl acetate copolymer, the gum base may optionally contain further synthetic elastomers in an amount of less than 10% by weight of the gum base polymers such as less than 8% by weight of the gum base polymers or less than about 5% by weight of the gum base polymers.

Such synthetic elastomers may be selected from the group consisting of styrene-butadiene copolymers (SBR), polyisobutylene, isobutylene-isoprene copolymers (IIR also known as butyl rubber, BR), polyurethane and polyethylene.

Preferred synthetic elastomers are styrene-butadiene copolymers (SBR), polyisobutylene and isobutylene-isoprene copolymers (BR).

If non-tack chewing gum is desired, copolymers of methyl vinyl ether and maleic acid and derivatives thereof, such as Gantrez and/or copolymers of polyisoprene-graft maleic anhydride (PIP-g-MA) with polyethylene-glycol (PEG) or methoxy-polyethylene-glycol (MPEG) side chains, such as REV-7 provided by Revolymer, may be among the gum base polymers.

The gum base matrix may further comprise:

0 to 40% by weight waxes, 5 to 35% by weight softeners other than waxes, such as plasticizers, fats and emulsifiers, 0 to 50% by weight filler, and 0 to 5% by weight of miscellaneous ingredients such as antioxidants, colorants, etc.

Natural resins are not used according to an embodiment of the invention, or at least only in minute amounts. According to an embodiment of the invention the medical chewing gum is free of natural rosin esters, often referred to as ester gums including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the medical chewing gum comprises further chewing gum ingredients selected from the group consisting of flavors, dry-binders, tableting aids, anti-caking agents, emulsifiers, antioxidants, enhancers, absorption enhancers, high intensity sweeteners, softeners, colors, active ingredients, water-soluble indigestible polysaccharides, water-insoluble polysaccharides or any combination thereof.

According to embodiments of the invention, said emulsifiers are selected from the group of cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sorbitan esters, diacetyl tartaric ester of monoglycerides, lactylated monoglycerides, mono- and/or di-glycerides of fatty acids such as glycerol monostearate, Acetem, lecithines or any combination thereof.

In an embodiment of the invention, said chewing gum comprises emulsifiers in an amount in the range of 0.1% to 25% by weight of said chewing gum.

In an embodiment of the invention the chewing gum comprises flavor. Flavor may typically be present in amounts between 0.01 and 10% by weight of the chewing gum, such as between 0.01 and 5% by weight of the chewing gum.

Non-exhaustive examples of flavors suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

Petroleum waxes aid in the curing of the finished gum made from the gum base as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes.

Petroleum wax (refined paraffin and microcrystalline wax) and paraffin wax are composed of mainly straight-chained normal-alkanes and branched iso-alkanes. The ratio of normal-alkanes to iso-alkanes varies.

The normal-alkanic waxes typically have carbon chain lengths >C-18 but the lengths are not predominantly longer than C-30. The branched and ring structures are located near the end of the chain for those waxes that are predominantly normal-alkanic. The viscosity of normal-alkanic waxes is <10 mm2/s (at 100° C.) and the combined number average molecular weight is <600 g/mole.

The iso-alkanic waxes typically have carbon lengths that are predominantly greater than C-30. The branched chains and ring structures are located randomly along the carbon chain in those waxes that are predominantly iso-alkanic. The viscosity of iso-alkanic waxes is greater than 10 mm2/s (at 100° C.) and the combined number average molecular weight is >600 g/mole.

Synthetic waxes are produced by means that are atypical for petroleum wax production and are thus not considered petroleum wax. The synthetic waxes may include waxes containing branched alkanes and copolymerized with monomers such as, but not limited to propylene, polyethylene, and Fischer Tropsch type waxes. Polyethylene wax is a synthetic wax containing alkane units of varying lengths having attached thereto ethylene monomers.

Waxes and fats are conventionally used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

Suitable vegetable oils include but are not limited to oils that are based on coconut, palm, palm kernel, cotton seed, rape seed or sunflower and combinations thereof.

Antioxidants prolong shelf life and storage of gum base, finished gum or their respective components including fats and flavor oils.

Antioxidants suitable for use in gum base include butylated hydroxyanisole (BHA), butylated hydroxytoluene (BHT), betacarotenes, tocopherols, acidulants such as Vitamin C (ascorbic acid or corresponding salts (ascorbates)), propyl gallate, other synthetic and natural types or mixtures thereof.

Further chewing gum ingredients, which may be included in the medical chewing gum according to the present invention, include surfactants and/or solubilizers. As examples of types of surfactants to be used as solubilizers in a medical chewing gum composition according to the invention, reference is made to H. P. Fiedler, Lexikon der Hilfstoffe für Pharmacie, Kosmetik and Angrenzende Gebiete, pages 63-64 (1981) and the lists of approved food emulsifiers of the individual countries. Anionic, cationic, amphoteric or non-ionic solubilizers can be used. Suitable solubilizers include lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene steraric acid esters.

Particularly suitable solubilizers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, block-copolymers of ethylene oxide and propyleneoxide and polyoxyethylene fatty alcohol ether. The solubilizer may either be a single compound or a combination of several compounds. In the presence of an active ingredient, such as the included one or more cannabinoids, the medical chewing gum may preferably also comprise a carrier known in the arts of chewing gum and pharmaceutical ingredients.

Poloxamer F68 is a further highly suitable solubilizer.

In some embodiments, one or more colors can be included in the chewing gum.

High intensity artificial sweetening agents can also be used according to preferred embodiments of the invention. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside and the like, alone or in combination.

In order to provide longer lasting sweetness and flavor perception, it may be desirable to encapsulate or otherwise control the release of at least a portion of the artificial sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the chewing gum.

A chewing gum and/or gum base may, if desired, include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, and combinations thereof.

According to an embodiment of the invention, one preferred filler/texturizer is calcium carbonate.

A number of chewing gum components well known within the art may be applied within the scope of the present invention. Such components comprise but are not limited to waxes, fats, softeners, fillers, bulk sweeteners, flavors, anti-oxidants, emulsifiers, coloring agents, binding agents and acidulants.

In an embodiment of the invention, the chewing gum is provided with an outer coating selected from the group consisting of hard coating, soft coating and edible film-coating or any combination thereof.

Cannabinoid may be attached to a carrier in an advantageous embodiment of the invention. One applicable carrier is microcrystalline cellulose.

Microcrystalline cellulose (MCC) may be prepared e.g. by hydrolyzing wood pulp by means of mineral acid. Thereby, microcrystalline cellulose may be obtained as purified, practically depolymerized cellulose. In more detail the manufacturing may typically comprise starting from selected rolls of wood pulp that are diced, or cut, into small particles. The chopped particles may then be hydrolyzed under heat and pressure by mineral acid. Thereafter, the obtained mixture may be washed and filtered.

Also, spray drying may be employed, which can be used to control the particle size distribution and the moisture content.

In some embodiments, microcrystalline cellulose may be obtained from other sources, such as other plant sources. Microcrystalline cellulose with different moisture content may be used. Typical moisture content may for example be about 5%, although other moisture contents, such as e.g. 3% or 1.5%, are also known to work.

Microcrystalline cellulose is commercially available, and may for example be obtained from FMC Biopolymer, e.g. the products known as Avicel PH 101, PH 102, PH 103, PH 105, PH 112, PH 113, PH 200, PH 301, and PH 302.

The chewing gum of the invention may be manufactured as an extruded chewing gum, or as a compressed chewing gum.

The chewing gum may be produced by a conventional batch or extrusion process. The process is well-known in the art. It should be noted that the temperature under which the one or more cannabinoids are added may advantageously be relatively low, e.g. be lower than 70 degrees Celsius When manufacturing a compressed chewing gum tablet another method is applied, which is basically very different than the extruded chewing gum, but may broadly be described as an initial conventional mixing of the gum base followed by a granulation of the obtained gum base mix. The obtained gum base granules may then be mixed with further chewing gum ingredients, such as sweeteners and flavor. This final granule mix may then be compressed under high pressure into a chewing gum tablet. For each compression a layer is made and in this way it is possible to make multi-layered chewing gums, such as two, three or four layers, wherein each layer may include an individual composition, e.g. cannabinoid or different colors may be used for visual purposes, etc.

The cannabinoid may advantageously be applied in a gum base-containing module or a tablet-module substantially free of gum base. In cases where a high initial release of cannabinoid is desired, the cannabinoid may advantageously be comprised in a tablet module substantially free of gum base whereas e.g. flavors and/or sweeteners advantageously may be added to the gum base-containing module and very often to both types of modules. The flavors and/or sweeteners may both be added as separate particles which are mixed and compressed with gum base-containing particles in one module and it may be incorporated into gum base-containing granules.

In some embodiments of the invention cannabinoids is carried by a carrier. Below the invention will be described with one particular carrier for exemplary purposes, although it should be noted that alternative carriers, such as sorbitol, may be applicable within the scope of the invention.

Referring to FIG. 1, a process for preparing a cannabinoid-microcrystalline cellulose mixture according to an embodiment of the invention is illustrated. The intention is to obtain a material, here cellulose, which comprises a well-defined amount of cannabinoid, salts thereof or derivatives thereof in and/or onto voids or pores within the material.

First a cannabinoid CAN is added to a mixer MIX1 together with microcrystalline cellulose MCC. The mixing ratio between the cannabinoid CAN and the microcrystalline cellulose may in some cases be around 1:1, but may generally vary from about 1:1000 to about 1:1.

The cannabinoid CAN may in some embodiments be cannabinoid as such or, and may in other embodiments be diluted cannabinoid. Diluted cannabinoid may often be simpler to handle, and/or easier to dose in accurate amounts. Examples of diluents may e.g. comprise one or more of propylene glycol, water, ethanol, or one or more solubilizers.

Optionally, one or more anti-oxidants may be added in the cannabinoid-MCC premix step, by adding the one or more anti-oxidants to the mixer MIX1 before, simultaneous with and/or after adding the one more cannabinoids and/or the carrier, such as e.g. microcrystalline cellulose MCC.

The mixer MIX1 may be any type of mixer capable of mixing the cannabinoid CAN and the microcrystalline cellulose MCC.

The mixer MIX1 is operated until an effective mixing of the cannabinoid CAN and the microcrystalline cellulose MCC is obtained.

Thereafter the resulting mixture of the cannabinoid CAN and the microcrystalline cellulose MCC may in some cases be subjected to a further processing PROC. This processing PROC may involve letting the mixture of the cannabinoid CAN and the microcrystalline cellulose MCC rest or soak for a period of time, e.g. in a sealed container, i.e. equilibrating the cannabinoid CAN and the microcrystalline cellulose MCC.

In some cases further mixing, either by means of mixer MIX1 or another mixer, may be employed.

In some cases the processing PROC may be carried out in the mixer MIX1, whereas in other cases the processing is carried out in separate process equipment. It may in some cases be especially advantageous to perform the processing PROC in the mixer MIX1 when further mixing is performed.

The final cannabinoid-microcrystalline cellulose mixture CC may be obtained from the processing PROC, if used, or from the mixer MIX1 if the processing PROC is not used.

Referring to FIG. 2, a process for preparing a chewing gum mass with cannabinoid-microcrystalline cellulose CMC according to an embodiment of the invention is illustrated.

Cannabinoid-microcrystalline cellulose mixture CC obtained in accordance with the embodiment illustrated on FIG. 1 may be used.

First, chewing gum ingredients CGI, including e.g. filler, is added to a mixer MIX2 together with a gum base GB and mixed therein to obtain a chewing gum mass CGM as a mixture of gum base and chewing gum ingredients GCI. The gum base must comprise an effective amount of gum base polymers. It is very important that the gum base is chosen such that the gum base polymers comprise polyvinyl acetate and vinyl laurate-vinyl acetate copolymer in an amount of more than 90% by weight of the gum base polymers. Similarly, the gum base should also be chosen such that the gum base polymers include 20-95% by weight of polyvinyl acetate and 5-80% by weight of vinyl laurate-vinyl acetate copolymer.

Then, the cannabinoid-microcrystalline cellulose mixture CC is added to a mixer MIX2 together with the chewing gum mass CGM. Thereby, a chewing gum mass with cannabinoid-microcrystalline cellulose CMC is obtained.

In some embodiments, the mixers MIX2 and MIX3 are different mixers, whereas in other embodiments they are the same mixer, but where timing divides the use of the mixer into two separate actions, first the mixing of the gum base GB with the chewing gum ingredients CGI, then mixing with the cannabinoid-MCC mixture CC.

The obtained chewing gum with cannabinoid-microcrystalline cellulose CMC may be used to produce chewing gum. In some embodiments further ingredients are added, e.g. further sweeteners, flavors, fillers etc. In other embodiments, such further ingredients, if needed, are all added to the gum base after adding the cannabinoid-MCC mixture.

The resulting chewing gum produced from the chewing gum mass with cannabinoid-microcrystalline cellulose CMC may be compressed chewing gum or extruded chewing gum.

When making compressed chewing gums, the cannabinoid premix may be added to gum base pellets together with other powders, such as e.g. sweeteners, fillers etc., and then compressed.

As illustrated in connection with FIGS. 1 and 2, MCC and cannabinoid are mixed and equilibrated. The cellulosic fiber and cannabinoid can be mixed in a suitable mixing device for any suitable length of time. In some cases, the cellulosic fiber and cannabinoid can be mixed with a mixing implement rotating at a speed of less than 500 rpm, less than 250 rpm, less than 150 rpm, less than 100 rpm, less than 60 rpm, less than 30 rpm, or less than 10 rpm. For example, the mixer can be a Kitchenaid, Hobart Mixer, ribbon blender, or other mixing apparatus depending on the desired batch size. In some cases, the MCC and cannabinoid can be mixed using a rotating and/or vibrating drum. In some cases, the cellulosic fibers and cannabinoid can be mixed for at least 1 minute, at least 3 minutes, at least 5 minutes, at least 10 minutes, or at 4 least 30 minutes prior to incorporating a resulting MCC-cannabinoid mixture into a chewing gum formulation or gum base formulation.

After mixing cellulosic fiber and cannabinoid, the cellulosic fiber-cannabinoid mixture can be equilibrated in a sealed container. In some cases, the sealed container can be a bag (e.g. a poly bag). In some cases, the MCC-cannabinoid mixture can be equilibrated for at least 30 minutes, at least 1 hour, at least 2 hours, at least 4 hours, at least 6 hours, at least 8 hours, or at least 10 hours prior to use or incorporation into an oral product. In some cases, a MCC-cannabinoid mixture can be further mixed or agitated during the equilibrating process. For example, a cellulosic fiber-cannabinoid mixture equilibrating in a poly bag can be agitated during the equilibrating process at a select time (e.g., 2 hours into the equilibrating process).

The following non-limiting examples illustrate different variations of the present invention. The examples are meant for indicating the inventive concept; hence the mentioned examples should not be understood as exhaustive for the present invention.

EXAMPLES

Example 1

Preparation of Cannabinoid Premix

A cannabinoid-microcrystalline cellulose (MCC) premix is made by first adding free cannabinoid to poloxamer F68 (PF) to obtain a 20% solution of cannabinoid in poloxamer F68. Butylated hydroxytoluene (BHT) is added (0.5%) to 50 grams of the cannabinoid-poloxamer F68 solid mix and added to 50 gram of microcrystalline cellulose provided as Avicel PH 102 from FMC Biopolymer. This is then mixed in a Kitchenaid mixer operated at about 30 RPM for about 30 minutes at room temperature. This mixture is equilibrated for about 30 minutes in a sealed container. Thereby, the cannabinoid-MCC mixture is obtained.

Example 2

Preparation of Cannabinoid Premix

A cannabinoid-MCC premix is made by adding first adding free cannabinoid to propylene glycol (PG) to obtain a 10% solution of cannabinoid in propylene glycol. 0.5% of butylated hydroxytoluene (BHT) is added to 50 grams of the cannabinoid-propylene glycol solution and then added to 50 gram of sorbitol. The cannabinoid-propylene glycol solution and the sorbitol are then mixed in a Kitchenaid mixer operated at about 30 RPM for about 30 minutes at room temperature. Finally, the obtained mixture of the cannabinoid-propylene glycol solution and the sorbitol is equilibrated for about 30 minutes in a sealed container. Thereby, the cannabinoid-MCC mixture is obtained.

Example 3

Composition of Gum Bases

Ten different gum bases (GB), given GB numbers 101-110, were prepared by the following process:

The polymers polyvinyl acetate (PVA), vinyl acetate-vinyl laurate copolymer (VA-VL), and optionally polyisobutylene (PIB) are mixed at 120° C. together with filler, here calcium carbonate or talc, in a mixer having horizontally placed Z-shaped arms for mixing.

When the polymers are softened, triacetin is added, followed by addition of emulsifier, wax and vegetable fat.

After a total mixing time of about 45-60 minutes, the mixture is discharged into a pan and allowed to cool to room temperature.

In case of example GB 108, comparative (comp.) example GB 109, and standard (Std.) gum base example GB 110, which include butyl rubber (BR), BR is added in the initial mixing step, and the mixing time is extended to a total of about 90-105 minutes.

In case of comparative (comp.) example GB 109, the natural resin is added before the addition of triacetin, and in case of standard (Std.) example GB 110, the natural resin is added after about 30 minutes before the addition of softeners.

The gum base compositions were as displayed in table 1A and 1B, the amounts given corresponding to percentages by weight of the gum base:

TABLE 1A

Gum base compositions, VA-VL I = vinyl acetate-vinyl laurate copolymer (Vinnapas B 500/40VL, supplied by Wacker); VA-VL II = vinyl acetate-vinyl laurate copolymer (Vinnapas B 500/20VL, supplied by Wacker); PVA I = polyvinyl acetate (Vinnapas B 1.5 sp, supplied by Wacker); PVA II = polyvinyl acetate (Vinnapas B 30 sp, supplied by Wacker); PIB = polyisobutylene (Oppanol B12, supplied by BASF); BR = butyl rubber (isobutylene-isoprene copolymer); Nat. resin = glycerol ester of hydrogenated gum rosin; Veg. fat = vegetable fat.

| | GB no. | | | | |
|---|---|---|---|---|---|
| | 101 | 102 | 103 | 104 | 105 |
| VA-VL I | 20 | — | 14 | — | 22 |
| VA-VL II | — | 20 | — | 22 | — |
| PVA I | 32 | 33 | 18 | 35 | 33 |
| PVA II | — | — | 5.0 | — | — |
| PIB | — | — | — | — | — |
| BR | — | — | — | — | — |
| Nat. resin | — | — | — | — | — |
| Calcium Carbonate | — | 19 | — | 22 | 17 |
| Talc | 20 | — | 41 | — | — |
| Triacetin | 8 | 8 | 6 | 7 | 2 |
| Emulsifier | 5 | 7 | 3 | 8 | 9 |
| Wax, microcrystalline | 13 | 13 | 10 | — | 12 |
| Veg. fat | 2 | — | 3 | 6 | 5 |
| Total | 100 | 100 | 100 | 100 | 100 |

TABLE 1B

Gum base compositions, VA-VL I = vinyl acetate-vinyl laurate copolymer (Vinnapas B 500/40VL, supplied by Wacker); VA-VL II = vinyl acetate-vinyl laurate copolymer (Vinnapas B 500/20VL, supplied by Wacker); PVA I = polyvinyl acetate (Vinnapas B 1.5 sp, supplied by Wacker); PVA II = polyvinyl acetate (Vinnapas B 30 sp, supplied by Wacker); PIB = polyisobutylene (Oppanol B12, supplied by BASF); BR = butyl rubber (isobutylene-isoprene copolymer); Nat. resin = glycerol ester of hydrogenated gum rosin; Veg. fat = vegetable fat.

| | GB no. | | | | |
|---|---|---|---|---|---|
| | 106 | 107 | 108 | 109 (comp.) | 110 (Std.) |
| VA-VL I | 21 | 20 | 20 | 10 | — |
| VA-VL II | — | — | — | — | — |
| PVA I | 31 | 30 | 30 | 20 | 25 |
| PVA II | — | — | — | — | — |
| PIB | 3.0 | 5.0 | 3.0 | 3.0 | 5 |
| BR | — | — | 2.0 | 2.0 | 5 |
| Nat. resin | — | — | — | 20 | 25 |
| Calcium Carbonate | 17 | 17 | 17 | 17 | 17 |
| Talc | — | — | — | — | — |
| Triacetin | 2 | 2 | 2 | 2 | — |
| Emulsifier | 9 | 9 | 9 | 9 | 5 |
| Wax, microcrystalline | 12 | 12 | 12 | 12 | 13 |
| Veg. fat | 5 | 5 | 5 | 5 | 5 |
| Total | 100 | 100 | 100 | 100 | 100 |

Example 4

Composition Cannabinoid Chewing Gum

Cannabinoid chewing gum were made as compressed gums, given CM numbers 1001-1010, 1011-1020 and 1021-1030, and as batch mixed gums, given CG numbers 1001-1010, 1011-1020 and 1021-1030, both using gum bases nos. 101-110 from Table 1 has the chewing gum compositions shown in table 2A-2F, the amounts given corresponding to percentages by weight of the chewing gum:

Cannabinoid is added as a 10% cannabinoid-MCC premix as disclosed in Example 1 resulting in a 1 gram chewing gum comprising 10 mg of cannabinoid.

TABLE 2A

Cannabinoid chewing gum compositions; MCC = microcrystalline cellulose. Liquid sweetener may for example be lycasin. Intense sweetener may for example be sucralose. Flavor may for example be pepper mint flavor.

| | CM and CG no. | | | | |
|---|---|---|---|---|---|
| | 1001 | 1002 | 1003 | 1004 | 1005 |
| GB 101 | 52 | — | — | — | — |
| GB 102 | — | 52 | — | — | — |
| GB 103 | — | — | 52 | — | — |
| GB 104 | — | — | — | 52 | — |
| GB 105 | — | — | — | — | 52 |
| GB 106 | — | — | — | — | — |
| GB 107 | — | — | — | — | — |
| GB 108 | — | — | — | — | — |
| GB 109 | — | — | — | — | — |
| GB 110 | — | — | — | — | — |
| Filler | 15 | 15 | 15 | 15 | 15 |
| Cannabinoid-MCC premix | 10.0 | 10.0 | 10.0 | 10.0 | 10.0 |
| Sodium hydrogen carbonate | 1.0 | 1.0 | 1.0 | 1.0 | 1.0 |
| Sodium carbonate | 2.0 | 2.0 | 2.0 | 2.0 | 2.0 |

TABLE 2A-continued

Cannabinoid chewing gum compositions; MCC = microcrystalline cellulose. Liquid sweetener may for example be lycasin. Intense sweetener may for example be sucralose. Flavor may for example be pepper mint flavor.

| | CM and CG no. | | | | |
|---|---|---|---|---|---|
| | 1001 | 1002 | 1003 | 1004 | 1005 |
| Sorbitol powder | 14 | 14 | 14 | 14 | 14 |
| Liquid sweetener | 1.5 | 1.5 | 1.5 | 1.5 | 1.5 |
| Intense sweetener | 0.4 | 0.4 | 0.4 | 0.4 | 0.4 |
| Flavor | 4.1 | 4.1 | 4.1 | 4.1 | 4.1 |
| Total | 100 | 100 | 100 | 100 | 100 |

TABLE 2B

Cannabinoid chewing gum compositions; MCC = microcrystalline cellulose. Liquid sweetener may for example be lycasin. Intense sweetener may for example be sucralose. Flavor may for example be pepper mint flavor.

| | CM and CG no. | | | | |
|---|---|---|---|---|---|
| | 1006 | 1007 | 1008 | 1009 (Comp.) | 1010 (Std.) |
| GB 101 | — | — | — | — | — |
| GB 102 | — | — | — | — | — |
| GB 103 | — | — | — | — | — |
| GB 104 | — | — | — | — | — |
| GB 105 | — | — | — | — | — |
| GB 106 | 52 | — | — | — | — |
| GB 107 | — | 52 | — | — | — |
| GB 108 | — | — | 52 | — | — |
| GB 109 | — | — | — | 52 | — |
| GB 110 | — | — | — | — | 52 |
| Filler | 15 | 15 | 15 | 15 | 15 |
| Cannabinoid-MCC premix | 10.0 | 10.0 | 10.0 | 10.0 | 10.0 |
| Sodium hydrogen carbonate | 1.0 | 1.0 | 1.0 | 1.0 | 1.0 |
| Sodium carbonate | 2.0 | 2.0 | 2.0 | 2.0 | 2.0 |
| Sorbitol powder | 14 | 14 | 14 | 14 | 14 |
| Liquid sweetener | 1.5 | 1.5 | 1.5 | 1.5 | 1.5 |
| Intense sweetener | 0.4 | 0.4 | 0.4 | 0.4 | 0.4 |
| Flavor | 4.1 | 4.1 | 4.1 | 4.1 | 4.1 |
| Total | 100 | 100 | 100 | 100 | 100 |

TABLE 2C

Cannabinoid chewing gum compositions; MCC = microcrystalline cellulose. Liquid sweetener may for example be lycasin. Intense sweetener may for example be sucralose. Flavor may for example be pepper mint flavor.

| | CM and CG no. | | | | |
|---|---|---|---|---|---|
| | 1011 | 1012 | 1013 | 1014 | 1015 |
| GB 101 | 52 | — | — | — | — |
| GB 102 | — | 52 | — | — | — |
| GB 103 | — | — | 52 | — | — |
| GB 104 | — | — | — | 52 | — |
| GB 105 | — | — | — | — | 52 |
| GB 106 | — | — | — | — | — |
| GB 107 | — | — | — | — | — |
| GB 108 | — | — | — | — | — |
| GB 109 | — | — | — | — | — |
| GB 110 | — | — | — | — | — |
| Filler | 16 | 16 | 16 | 16 | 16 |
| Cannabinoid-MCC premix | 9 | 9 | 9 | 9 | 9 |

TABLE 2C-continued

Cannabinoid chewing gum compositions; MCC = microcrystalline cellulose. Liquid sweetener may for example be lycasin. Intense sweetener may for example be sucralose. Flavor may for example be pepper mint flavor.

| | CM and CG no. | | | | |
|---|---|---|---|---|---|
| | 1011 | 1012 | 1013 | 1014 | 1015 |
| Sodium hydrogen carbonate | 1.0 | 1.0 | 1.0 | 1.0 | 1.0 |
| Sodium carbonate | 2.0 | 2.0 | 2.0 | 2.0 | 2.0 |
| Sorbitol powder | 14 | 14 | 14 | 14 | 14 |
| Liquid sweetener | 1.5 | 1.5 | 1.5 | 1.5 | 1.5 |
| Intense sweetener | 0.4 | 0.4 | 0.4 | 0.4 | 0.4 |
| Flavor | 4.1 | 4.1 | 4.1 | 4.1 | 4.1 |
| Total | 100 | 100 | 100 | 100 | 100 |

TABLE 2D

Cannabinoid chewing gum compositions; MCC = microcrystalline cellulose. Liquid sweetener may for example be lycasin. Intense sweetener may for example be sucralose. Flavor may for example be pepper mint flavor.

| | CM and CG no. | | | | |
|---|---|---|---|---|---|
| | 1016 | 1017 | 1018 | 1019 (Comp.) | 1020 (Std.) |
| GB 101 | — | — | — | — | — |
| GB 102 | — | — | — | — | — |
| GB 103 | — | — | — | — | — |
| GB 104 | — | — | — | — | — |
| GB 105 | — | — | — | — | — |
| GB 106 | 52 | — | — | — | — |
| GB 107 | — | 52 | — | — | — |
| GB 108 | — | — | 52 | — | — |
| GB 109 | — | — | — | 52 | — |
| GB 110 | — | — | — | — | 52 |
| Filler | 16 | 16 | 16 | 16 | 16 |
| Cannabinoid-MCC premix | 9 | 9 | 9 | 9 | 9 |
| Sodium hydrogen carbonate | 1.0 | 1.0 | 1.0 | 1.0 | 1.0 |
| Sodium carbonate | 2.0 | 2.0 | 2.0 | 2.0 | 2.0 |
| Sorbitol powder | 14 | 14 | 14 | 14 | 14 |
| Liquid sweetener | 1.5 | 1.5 | 1.5 | 1.5 | 1.5 |
| Intense sweetener | 0.4 | 0.4 | 0.4 | 0.4 | 0.4 |
| Flavor | 4.1 | 4.1 | 4.1 | 4.1 | 4.1 |
| Total | 100 | 100 | 100 | 100 | 100 |

TABLE 2E

Cannabinoid chewing gum compositions; MCC = microcrystalline cellulose. Liquid sweetener may for example be lycasin. Intense sweetener may for example be sucralose. Flavor may for example be pepper mint flavor.

| | CM and CG no. | | | | |
|---|---|---|---|---|---|
| | 1021 | 1022 | 1023 | 1024 | 1025 |
| GB 101 | 52 | — | — | — | — |
| GB 102 | — | 52 | — | — | — |
| GB 103 | — | — | 52 | — | — |
| GB 104 | — | — | — | 52 | — |
| GB 105 | — | — | — | — | 52 |
| GB 106 | — | — | — | — | — |
| GB 107 | — | — | — | — | — |
| GB 108 | — | — | — | — | — |
| GB 109 | — | — | — | — | — |
| GB 110 | — | — | — | — | — |

TABLE 2E-continued

Cannabinoid chewing gum compositions; MCC = microcrystalline cellulose. Liquid sweetener may for example be lycasin. Intense sweetener may for example be sucralose. Flavor may for example be pepper mint flavor.

| | CM and CG no. | | | | |
|---|---|---|---|---|---|
| | 1021 | 1022 | 1023 | 1024 | 1025 |
| Filler | 14 | 14 | 14 | 14 | 14 |
| Cannabinoid-MCC premix | 11 | 11 | 11 | 11 | 11 |
| Sodium hydrogen carbonate | 1.0 | 1.0 | 1.0 | 1.0 | 1.0 |
| Sodium carbonate | 2.0 | 2.0 | 2.0 | 2.0 | 2.0 |
| Sorbitol powder | 14 | 14 | 14 | 14 | 14 |
| Liquid sweetener | 1.5 | 1.5 | 1.5 | 1.5 | 1.5 |
| Intense sweetener | 0.4 | 0.4 | 0.4 | 0.4 | 0.4 |
| Flavor | 4.1 | 4.1 | 4.1 | 4.1 | 4.1 |
| Total | 100 | 100 | 100 | 100 | 100 |

TABLE 2F

Cannabinoid chewing gum compositions; MCC = microcrystalline cellulose. Liquid sweetener may for example be lycasin. Intense sweetener may for example be sucralose. Flavor may for example be pepper mint flavor.

| | CM and CG no. | | | | |
|---|---|---|---|---|---|
| | 1026 | 1027 | 1028 | 1029 (Comp.) | 1030 (Std.) |
| GB 101 | — | — | — | — | — |
| GB 102 | — | — | — | — | — |
| GB 103 | — | — | — | — | — |
| GB 104 | — | — | — | — | — |
| GB 105 | — | — | — | — | — |
| GB 106 | 52 | — | — | — | — |
| GB 107 | — | 52 | — | — | — |
| GB 108 | — | — | 52 | — | — |
| GB 109 | — | — | — | 52 | — |
| GB 110 | — | — | — | — | 52 |
| Filler | 14 | 14 | 14 | 14 | 14 |
| Cannabinoid-MCC premix | 11 | 11 | 11 | 11 | 11 |
| Sodium hydrogen carbonate | 1.0 | 1.0 | 1.0 | 1.0 | 1.0 |
| Sodium carbonate | 2.0 | 2.0 | 2.0 | 2.0 | 2.0 |
| Sorbitol powder | 14 | 14 | 14 | 14 | 14 |
| Liquid sweetener | 1.5 | 1.5 | 1.5 | 1.5 | 1.5 |
| Intense sweetener | 0.4 | 0.4 | 0.4 | 0.4 | 0.4 |
| Flavor | 4.1 | 4.1 | 4.1 | 4.1 | 4.1 |
| Total | 100 | 100 | 100 | 100 | 100 |

Example 5

Preparation of Batch Mixed Cannabinoid Chewing Gum

Gum base and filler according to Example 4 are mixed in a mixer having horizontally placed Z-shaped arms for mixing. The mixer was preheated to a temperature of up to approximately 50° C. When the content of the mixer is homogeneous, the other ingredients according to Example 4 are added according to a specified time schedule. The processed compositions are finally cut into conventionally mixed chewing gum cores CM1001-CM1010, CM1011-CM1020 and CM1021-CM1030. The process corresponds largely to the process disclosed in international patent application WO 02/076230 A1, hereby incorporated by reference.

Example 6

Preparation of Compressed Cannabinoid Chewing Gum

Gum base and filler according to Example 4 formed into gum base granules by a granulation process. The cannabinoid premix is then adsorbed to the gum base granules, optionally together with other liquid chewing gum ingredients. The other ingredients according to Example 4 are mixed with the gum base particles into a homogeneous mix of gum base granules and chewing gum particles. The mixed gum base granules and chewing gum ingredients are then compressed into chewing gum tablets CG1001-CG1010, CG1011-CG1020 and CG1021-CG1030. Liquid ingredients may in some cases be mixed into the gum base. The process corresponds largely to the process disclosed in international patent application WO 2004/004479 A1, hereby incorporated by reference.

Example 7

Evaluation of Cannabinoid Chewing Gum

Different examples of the medical chewing gum were evaluated with respect to stability, texture, robustness, release of flavor and cannabinoid, taste profile and other important features.

The medical chewing gum is highly suitable as delivery vehicle for cannabinoid.

LIST OF FIGURE REFERENCES

CAN. Cannabinoids
MCC. Microcrystalline cellulose
MIX1. Mixer
MIX2. Mixer
MIX3. Mixer
PROC. Processing
CC. Cannabinoid-microcrystalline cellulose mixture
GB. Gum base
CGI. Chewing gum ingredients
CGM. Chewing gum mass
CMC. Chewing gum mass with cannabinoid-microcrystalline cellulose mixture

The invention claimed is:

1. A medical chewing gum comprising gum base polymers and one or more cannabinoids as an active pharmaceutical ingredient, wherein
    the gum base polymers comprise polyvinyl acetate and vinyl laurate-vinyl acetate copolymer in an amount of more than 90% by weight of the gum base polymers, and
    the gum base polymers include 20-95% by weight of polyvinyl acetate and 5-80% by weight of vinyl laurate-vinyl acetate copolymer,
    wherein the chewing gum is a compressed chewing gum comprising granules with a content of gum base and extragranular chewing gum ingredients.

2. The medical chewing gum according to claim 1, wherein the total content of gum base ingredients selected from the list consisting of polyterpene resins, resins based on gum rosin, wood rosin and tall oil resin is less than 5 percent by weight of the chewing gum.

3. The medical chewing gum according to claim 1, wherein the chewing gum contains no polyterpene resins and no resins based on gum rosin, wood rosin or tall oil resin.

4. The medical chewing gum according to claim 1, wherein the one or more cannabinoids is a least partly comprised in said granules.

5. The medical chewing gum according to claim 1, the one or more cannabinoids is a least partly comprised outside the granules.

6. The medical chewing gum according to claim 1, wherein said medical chewing gum comprises gum base granules, said gum base granules comprising gum base polymers.

7. The medical chewing gum according to claim 1, wherein the one or more cannabinoids comprises THC, CBD, and salts, derivatives, analogues and homologues thereof.

8. The medical chewing gum according to claim 1, wherein said chewing gum comprises said cannabinoids in an amount of 0.1-30 mg.

9. The medical chewing gum according to claim 1, wherein the one or more cannabinoids is at least partly contained in a carrier.

10. The medical chewing gum according to claim 1, wherein the chewing gum comprises cellulose as a carrier for said one or more cannabinoids.

11. The medical chewing gum according to claim 10, wherein said carrier cellulose is or comprises microcrystalline cellulose (MCC).

12. The medical chewing gum according to claim 10, wherein said carrier cellulose is provided in the form of particles having an average particle size between 10 and 250 micrometers.

13. The medical chewing gum according to claim 1, wherein said medical chewing gum comprises one or more fillers, wherein said one or more fillers comprises cellulose.

14. The medical chewing gum according to claim 1, wherein the medical chewing gum is substantially free of natural resins.

15. The medical chewing gum according to claim 1, wherein the chewing gum comprises gum base polymers in an amount of between 15 and 80 percent by weight of the chewing gum.

16. The medical chewing gum according to claim 1, wherein the gum base polymers consist of synthetic gum base polymers.

17. The medical chewing gum according to claim 1, wherein the weight ratio between the polyvinyl acetate and the vinyl laurate-vinyl acetate copolymer is from 8:1 to 2:3.

18. The medical chewing gum according to claim 1, wherein the weight ratio between the polyvinyl acetate and the vinyl laurate-vinyl acetate copolymer is from 5:1 to 2:3.

19. The medical chewing gum according to claim 1, wherein the weight ratio between the polyvinyl acetate and the vinyl laurate-vinyl acetate copolymer is from 3:2 to 2:3.

20. The medical chewing gum according to claim 1, wherein the weight ratio between vinyl acetate monomers of the vinyl laurate-vinyl acetate copolymer and vinyl laurate monomers of the vinyl laurate-vinyl acetate copolymer is less than 90:10.

21. The medical chewing gum according to claim 1, wherein the total release of the one or more cannabinoids is increased compared to conventional extruded chewing gum.

22. The medical chewing gum according to claim 1, wherein the release rate of the one or more cannabinoids is increased compared to conventional extruded chewing gum.

23. The medical chewing gum according to claim 1, wherein initial crumbling of the gum facilitates increased total release of the one or more cannabinoids compared to conventional extruded chewing gum.

24. A medical chewing gum comprising gum base polymers and one or more cannabinoids as an active pharmaceutical ingredient, wherein
   the gum base polymers constitute more than 50% by weight of the total content of gum base ingredients,
   the total content of gum base ingredients selected from the list consisting of polyterpene resins, resins based on gum rosin, wood rosin and tall oil resin is less than 5% by weight of the chewing gum, and
   the gum base polymers include 20-95% by weight of polyvinyl acetate and 5-80% by weight of vinyl laurate-vinyl acetate copolymer,
   wherein the chewing gum is a compressed chewing gum comprising granules with a content of gum base and extragranular chewing gum ingredients.

25. The medical chewing gum according to claim 24, wherein the gum base polymers substantially consist of synthetic gum base polymers.

26. A medical chewing gum comprising gum base with a content of gum base polymers and one or more cannabinoids as an active pharmaceutical ingredient, wherein
   the gum base comprises 15-45% by weight of polyvinyl acetate and 10-30% by weight of vinyl laurate-vinyl acetate copolymer,
   the total content of gum base ingredients selected from the list consisting of polyterpene resins, resins based on gum rosin, wood rosin and tall oil resin is less than 5% by weight of the chewing gum, and
   the gum base polymers include 20-95% by weight of polyvinyl acetate and 5-80% by weight of vinyl laurate-vinyl acetate copolymer,
   wherein the chewing gum is a compressed chewing gum comprising granules with a content of gum base and extragranular chewing gum ingredients.

27. The medical chewing gum according to claim 26, wherein the medical chewing gum is substantially free of natural resins.

* * * * *